(12) United States Patent
Velez-Rivera

(10) Patent No.: US 10,463,818 B2
(45) Date of Patent: Nov. 5, 2019

(54) MULTIPLE CONNECTOR DEVICE FOR RESPIRATORY CIRCUITS WITH ALARM DUE TO DISCONNECTION

(76) Inventor: Héctor de Jesús Velez-Rivera, Jalisco (MX)

( * ) Notice: Subject to any disclaimer, the term of this patent is extended or adjusted under 35 U.S.C. 154(b) by 1465 days.

(21) Appl. No.: 14/381,471

(22) PCT Filed: Mar. 1, 2012

(86) PCT No.: PCT/IB2012/000388
§ 371 (c)(1),
(2), (4) Date: Dec. 2, 2014

(87) PCT Pub. No.: WO2013/128221
PCT Pub. Date: Sep. 6, 2013

(65) Prior Publication Data
US 2015/0083122 A1 Mar. 26, 2015

(51) Int. Cl.
*A61M 16/00* (2006.01)
*A61M 16/08* (2006.01)
*A61M 16/10* (2006.01)

(52) U.S. Cl.
CPC .... *A61M 16/0051* (2013.01); *A61M 16/0816* (2013.01); *A61M 16/0833* (2014.02);
(Continued)

(58) Field of Classification Search
CPC .......... A61M 16/0051; A61M 16/0003; A61M 16/0833; A61M 16/0841; A61M 16/085;
(Continued)

(56) References Cited

U.S. PATENT DOCUMENTS 3,556,097 A 1/1971 Wallace
4,067,329 A 1/1978 Winicki
(Continued)

FOREIGN PATENT DOCUMENTS

EP 0 742 027 A2 11/1996
EP 0742027 A2 * 11/1996 ............ A61M 16/08
(Continued)

OTHER PUBLICATIONS

International Search Report dated Nov. 20, 2012 issued in corresponding International patent application No. PCT/IB2012/000388.

*Primary Examiner* — Jan Christopher L Merene
*Assistant Examiner* — Elliot S Ruddie
(74) *Attorney, Agent, or Firm* — Ostrolenk Faber LLP

(57) ABSTRACT

The present invention relates to a multiple connector device for respiratory circuits with alarm due to disconnection, which comprises a main body which is hollow inside, which is in the form of a cross having four arms which are: an upper vertical tubular arm inside of which is housed a driving element which projects into the interior of the lower vertical arm; a lower vertical arm preferably of a square form, which is partially hollow in the interior thereof for the purpose of housing a segment of the driving element and a control element; a right lateral arm; and a left lateral arm which is a mirror image of the right lateral arm, wherein the driving element is in the form of an arrow that effects an axial movement along the upper vertical arm and the lower vertical arm of the main body and the control element is an electronic board that includes all of the electronic components for operating the multiple connector device and which together with the arrangement of the driving element enable the proper functioning thereof.

20 Claims, 6 Drawing Sheets

(52) U.S. Cl.
CPC ..... *A61M 16/085* (2014.02); *A61M 2016/103* (2013.01); *A61M 2202/0241* (2013.01); *A61M 2205/14* (2013.01); *A61M 2205/15* (2013.01); *A61M 2205/18* (2013.01); *A61M 2205/3317* (2013.01); *A61M 2205/581* (2013.01); *A61M 2205/583* (2013.01); *A61M 2205/8206* (2013.01); *A61M 2230/432* (2013.01)

(58) Field of Classification Search
CPC .. A61M 16/1005; A61M 16/04; A61M 16/06; A61M 16/0816; A61M 16/104; A61M 2016/1025; A61M 2016/103; A61M 2202/0241; A61M 2205/14; A61M 2205/15; A61M 2205/18; A61M 2205/33; A61M 2205/3303; A61M 2205/3306; A61M 2205/3317; A61M 2205/35; A61M 2205/581; A61M 2205/583; A61M 2205/82; A61M 2205/8206; A61M 2209/06; A61M 2209/08; A61M 2230/432; A61M 2230/435
See application file for complete search history.

(56) References Cited

U.S. PATENT DOCUMENTS

| | | |
|---|---|---|
| 4,506,665 A | 3/1985 | Andrews et al. |
| 5,062,420 A | 11/1991 | Levine |
| 5,661,231 A | 8/1997 | Koskela |
| 6,679,432 B1 | 1/2004 | Arnold |
| 2008/0264413 A1 | 10/2008 | Doherty et al. |
| 2015/0306323 A1* | 10/2015 | Buenafe ............ A61M 16/0051 128/202.22 |

FOREIGN PATENT DOCUMENTS

| | | |
|---|---|---|
| ES | 0 444 404 A1 | 5/1977 |
| WO | WO 2005/035365 A1 | 4/2005 |

* cited by examiner

MULTIPLE CONNECTOR DEVICE FOR RESPIRATORY CIRCUITS WITH ALARM DUE TO DISCONNECTION

TECHNICAL FIELD

The present invention relates to the techniques used in the design and manufacture of devices used in therapeutic and surgical procedures in Medicine that are used for fastening and securing auxiliary elements of respiratory or anesthesia circuits, and more specifically, the invention is related to a multiple connector device for respiratory circuits with alarm due to disconnection.

BACKGROUND OF THE INVENTION

Breathing circuits, also called anesthetic circuits, comprise a set of elements that allow gases and/or anesthetic vapors to be conducted from an anesthesia machine to a patient, so that a gas exchange with the exterior occurs. The function of the elements of the breathing circuit is not only to allow a proper administration of the anesthetic via the lungs but also provide oxygen and remove carbon dioxide in a suitable manner. Some of the elements of the breathing circuit are ringed or corrugated tubes, reservoir bags, overflow valves and/or directional valves, anesthesia machines, filters, connectors and oxygen masks among others elements.

Nowadays, when a patient undergoes a surgical procedure where the use of an anesthesia circuit is required, there is a risk that some of the elements of the circuit are disconnected, without the medical staff being aware of this situation, that results in a leakage of the anesthetic gas that does not cause immediate damage to the medical staff, nevertheless, if this situation repeatedly occurs it may cause serious damage to their health.

There are devices in the prior art that trigger an alarm in case of disconnection of an element to which they are attached, such as the device of Spanish patent application No. ES 0 444 404 A1, which comprises a pneumatic device that emits both a visual and an audible alarm when there is a disconnection of a tube previously inserted into another. In particular, the device is mainly focused on the disconnection of the tube that is directed to the endotracheal cannula of a breathing apparatus that allows the patient's breathing. To achieve this objective, said device comprises a pneumatic supply, a pneumatic switch, a filter, an adjustable decompressor, an "on-off"-type magnetic cell, which is fed by the power supply and is driven due to a pressure change in a capture tube, a distributor, an audio apparatus and a pneumo-electric switch. The capture tube should be inserted between the walls of the endotracheal cannula and the respiratory apparatus of the patient in order to operate the device. When there is a disconnection of the cannula, the tube that was previously pressurized, undergoes a pressure variation and a pressure decreasing which causes the pneumatic cell to tilt and the operative position of the distributor is initiated so that the activation of both audible and visual alarms happens.

However, since this device is pneumatic, the same has the disadvantage that requires a constant supply of air. Likewise, the pneumatic cell should be housed within a closed box to reduce noise that is caused by the exhausting of the gas during the operation of the device, which makes the device inconvenient for those patients that require the use of the same.

Another prior art example of elements that indicate leakage of anesthetic gas is that disclosed in U.S. Pat. No. 5,661,231 in which, it is revealed an arrangement for detecting filtrations or leaks in respiratory circuits by means of the use of a device designed for such purpose. Said device comprises two elements: a connector and a closure element. The connector has a "Y" form and is attached to the anesthesia machine that is part of the breathing circuit. The closure member has a cylindrical shape for allowing its insertion into the connector that is hollow inside. Also, the device comprises detection means on its outer surface that sends an electrical signal in case said two elements are decoupled. The detection means comprises, in turn, a button and a micro-switch located at the lower part of the button.

The operation of the above mentioned device is as follows: when the closure member is inserted into the connector, the button, which is located on the outer surface of the closure member, is pushed down in order to actuate the micro-switch. The micro-switch sends a signal to the anesthesia machine that constantly monitors said condition. If these elements are decoupled, the micro-switch is disabled so that the anesthesia machine emits an alarm signal indicating said decoupling.

One of the disadvantages of the device disclosed in US Patent '231, is that, all the time, an electrical connection should be present between the device and the anesthesia machine in order to emit the corresponding alarm. Since, a wired connection is permanently present between said two elements; there is a risk of inadvertent disconnection if the patient is moved. It is desirable that this type of device is provided with a portable power supply (battery) to achieve autonomy and provide greater comfort to patients and the medical staff. Also, another disadvantage of this device, is its possible incompatibility with other models of anesthesia machines of a given hospital.

In the medical field, and more specifically in the area of surgery, a major concern is intra-hospital contagious when using respiratory circuits including anesthesia machines, since some elements are reused. In order to eliminate this drawback, the invention of U.S. Pat. No. 3,556,097 is mainly based on the manufacture of the breathing circuit elements whose production costs are reduced and thus to be disposable leading to an improved hygiene in breathing circuits.

The above mentioned invention comprises a respiratory mask, collapsible conduits, an interconnecting device between the conduits and the breathing mask; a breathing bag and a filter. More particularly, the interconnecting device has a "T" form; so that at the lower end thereof it is coupled a breathing mask or an endotracheal cannula; while the lateral ends thereof are designed to connect foldable pipes, the device is characterized because there is a rotational movement between the device and the connected tubes, resulting in a greater comfort to the patient.

However, this patent document only mentions elements of the breathing circuit, but fails to mention any device or element which indicates to the patient or the medical staff if the components of the circuit are disconnected.

As it can observed from the above, in the prior art there is disclosed the use of interconnection devices to be coupled to respiratory or anesthesia circuits in order to facilitate its handling during surgery; however, these connecting devices of the prior art have the disadvantage that they do not include any element indicating to the medical staff if the breathing circuit is disconnected resulting in the leakage of anesthetic gas.

Consequently, it has been sought to overcome the drawbacks of the prior art by developing a multiple connector device for respiratory circuits with alarm due to disconnection.

SUMMARY OF THE INVENTION

The present invention relates to a multiple connector device for respiratory circuits with alarm due to disconnection, the device comprises in general terms: a main body having a cross form with four arms, namely an upper vertical arm, a lower vertical arm, and right lateral arm and left lateral arm.

The upper vertical arm has a tubular form and is sectioned along its length, defining three different sections each having a different diameter with respect the other, namely: a distal section, a middle section and a proximate section. In addition, on the inner wall of the distal section of the upper vertical arm, there is provided a first gasket having the shape of a cylindrical ring and a length that is less than the total length of the distal section.

Additionally, on the outer front surface of the proximate section, there is provided a hollow tube that is upwardly projected thereto, the hollow tube is threaded at the distal end thereof and is used for capnography of the user of the device of the instant invention. When said hollow tube is not in use, a cap is threaded to the same, the cap comprises a central hollow body having a cylindrical shape; a plurality of supports radially disposed and downwardly running from the top of said central hollow body; and a solid post which projects downwardly from the upper wall of the inner portion of said central hollow body.

On the other hand, the lower vertical arm has a square shape, inside which a guide duct runs along the entire total of the lower vertical arm. The guide duct is aligned with the longitudinal axis of the upper vertical arm. The upper face of said lower vertical arm comprises a low-relief area and a no-relief area. In addition, the low-relief area includes a rectangular hole through which the guide conduct passes; and an opening for accessing into said lower vertical arm.

Above the low-relief area, there is provided a sliding cover that longitudinally slides (up and down) over said area. The relative position of the sliding cover with respect to the low-relief area indicates the user if the multiple connector device is in the "on" or "off" position. In addition, in order to hold the sliding cover to the low-relief area, the sliding cover has a locking tab that is preferably located on a lateral edge of the sliding cover. Adjacent to low-relief area and over the outer face of the lower vertical arm, there is provided a grid which allows acoustic communication between the interior of said lower vertical arm and the outside of the device.

The lower face of the lower vertical arm comprises a protecting hollow cover, which has a plurality of guide reinforcements on its inner peripheral edge which provides greater rigidity and strength, the reinforcements are used to keep the control element that is housed inside in place.

Regarding the right lateral arm, the same has a tubular shape and has a constant inner diameter along all its length. At its distal end, said right lateral arm has a first peripheral flange. Adjacent to the first peripheral flange, there is provided a first recess that is designed to house a second gasket. Also, toward the center of the multiple connector device, there is provided a first stop surrounding the entire circumference of the right lateral arm. The left lateral arm is a mirror image of the right lateral arm and has the same elements and configuration as the right lateral arm.

A driving element axially runs along the inside of the upper vertical arm as well as the lower vertical arm of the main body; the driving element has the shape of a flattened arrow and comprises a tip, a stem and a stabilizer. The tip is hollow inside in order to house a sensing element that is selected from a magnet, a capacitive piece or a magnetic core. The orientation of the driving element into the main body is axial and longitudinal, that is to say, the tip coincides with the distal end of the lower vertical arm while the stabilizer coincides with the distal end of the upper vertical arm.

Finally, the control element comprises an electronic board which along with the driving element comprises electronic components that are required by the multiple connector device in order to properly perform its functions. Among, said electronic components there is a plurality of light emitting diodes, a plurality of resistors, a central switch that is actuated by a magnetic field, a sliding switch, a speaker and a battery.

The multiple connector device of the present invention is used in those surgical procedures where it is required connecting the patient to an anesthesia circuit. The multiple connector device is connected to a device for controlling the airways in a patient through the upper vertical arm, while each of the right and left lateral arms is connected to a corrugated tube by means of a rotary connector, said corrugated tubes being part of an anesthesia circuit.

In order to carry out the above, the first gasket located on the inner part of the distal section of the upper vertical arm achieves a tight seal with the device to control the airways. Likewise, the second gasket located on the outer surface of the right lateral arm and the left lateral vertical arm allows a tight seal with the connectors of the corrugated tubes of the anesthesia circuit thus avoiding leakages of the anesthetic gas during surgery.

BRIEF DESCRIPTION OF THE DRAWINGS

The novel aspects that are considered characteristic of this invention are set forth with particularity in the appended claims. However, the invention itself, both by its structure and its operation, together with other objects and advantages thereof, will be best understood from the following detailed description of a preferred embodiment when read in conjunction with the accompanying drawings, in which:

OBJECTS OF THE INVENTION

Figure 1:
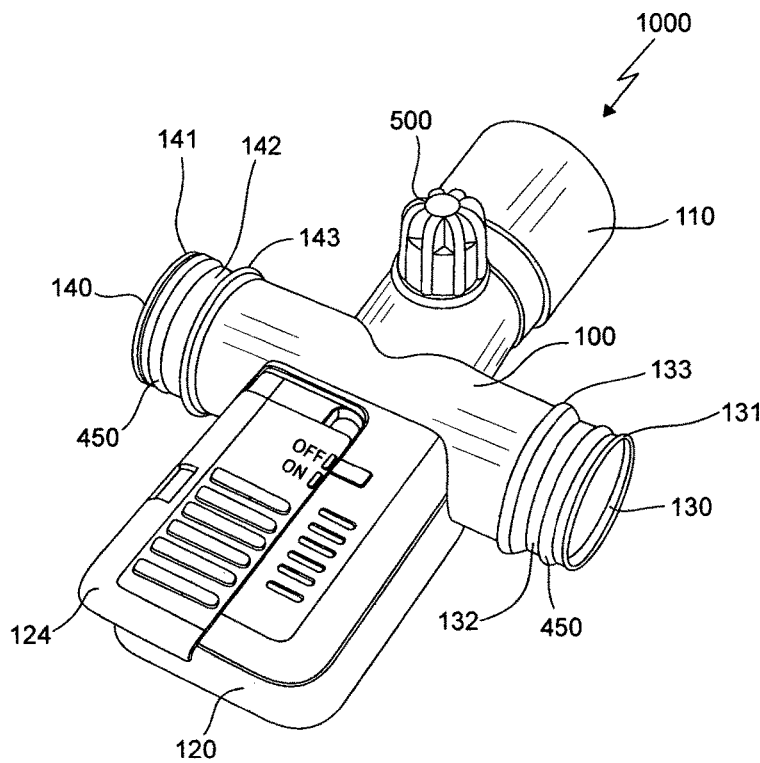
FIG. 1 is a side perspective view of a multiple connector device for respiratory circuits with alarm due to disconnection built in accordance with the principles of a particularly preferred embodiment of the present invention.
Figure 2:
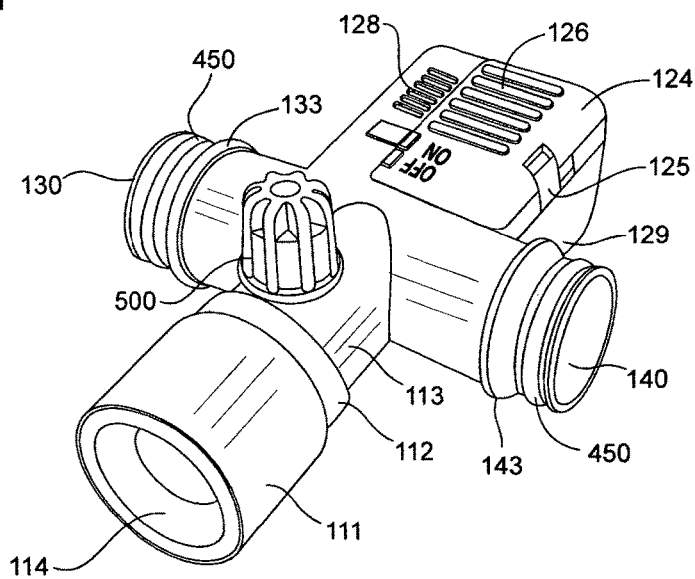
FIG. 2 is a side perspective view being rotated 180° with respect to the view shown in FIG. 1 of the multiple connector device for respiratory circuits with alarm due to disconnection.

Having in mind the drawbacks of the prior art, an object of the present invention is to provide a multiple connector device for respiratory circuits with alarm due to disconnection having a functional design and being of simple manufacturing, yet the device being highly effective in detecting disconnection problems of the auxiliary devices that allow and/or facilitate the breathing of a patient, avoiding in this way the presence of anesthetic gas leaks during surgery.

It is another object of the present invention to provide a multiple connector device for respiratory circuits with alarm due to disconnection, which provides a visual and a sound alarm signal in case of disconnection of the auxiliary devices and to alert the medical staff about the unwanted decoupling.

It is still another object of the present invention to provide a multiple connector device for respiratory circuits with alarm due to disconnection, allowing and effective and easy coupling of those devices for controlling the airways of a patient during a surgical procedure, such as oxygen masks, endotracheal cannulas and/or laryngeal masks.

It is an object of the present invention to provide a multiple connector device for respiratory circuits with alarm due to disconnection that allows a secure and effective coupling with rotary-type connectors that are connected to corrugated tubes in order to obtain a greater capacity of rotational movement, thus facilitating their final orientation.

A further object of the present invention is to provide a multiple connector device for respiratory circuits with alarm due to disconnection, whose manufacture is inexpensive, disposable and non-toxic.

Yet another object of the present invention is to provide a multiple connector device for respiratory circuits with alarm due to disconnection, having a long lasting performance without requiring substitutions or replacements of the components that are part of the same.

DETAILED DESCRIPTION OF THE INVENTION

Referring now to the accompanying drawings, and more specifically to FIGS. 1-5 thereof that illustrate a multiple connector device for respiratory circuits with alarm due to disconnection 1000 built in accordance with a particularly preferred embodiment of the present invention, which should be regarded as illustrative but no limitative of the invention, the multiple connector device for respiratory circuits with alarm due to disconnection 1000 comprises, in general terms, a main body 100 which is hollow inside and has the shape of a cross defining four arms namely an upper vertical arm 110 having a tubular form, within which there is housed a driving element 200 which projects into the inside of a lower vertical arm 120 that has a square form and is partially hollow inside in order to house a portion of the driving element 200 and a control element 300; a right lateral arm 130 having a tubular form; and a left lateral arm 140 that is a mirror image of the right lateral arm 130.

The driving element 200 has the shape of an arrow which has an axial movement along the upper vertical arm 110 and the lower vertical arm 120.

The control element 300 is an electronic board that includes electronics components of the multiple connector device 1000 and with the driving element 200 are configured to allow the proper functioning of the multiple connector device 1000.

The upper vertical arm 110 is tubular in shape and is sectioned longwise defining three different sections, each being of a different diameter with respect the other, namely: a distal section 111 which has the largest diameter and extends from the distal edge thereof to about two-fifths of the total length of the upper arm toward the center of the main body; a middle section 112 located adjacent to the distal section 111, the middle section has an outer diameter and an inner diameter smaller than those of the distal section 111, the middle section extents about a fifth of the total length of the upper vertical arm 110 running in the direction the center of the main body; and, an proximate section 113 that is located adjacent to the middle section 112, the proximate section has an outer diameter smaller than that of the middle section 112 but having an inner diameter equal to that of the middle section 112, said proximate section 113 extending until the center of the main body.

Figure 3:
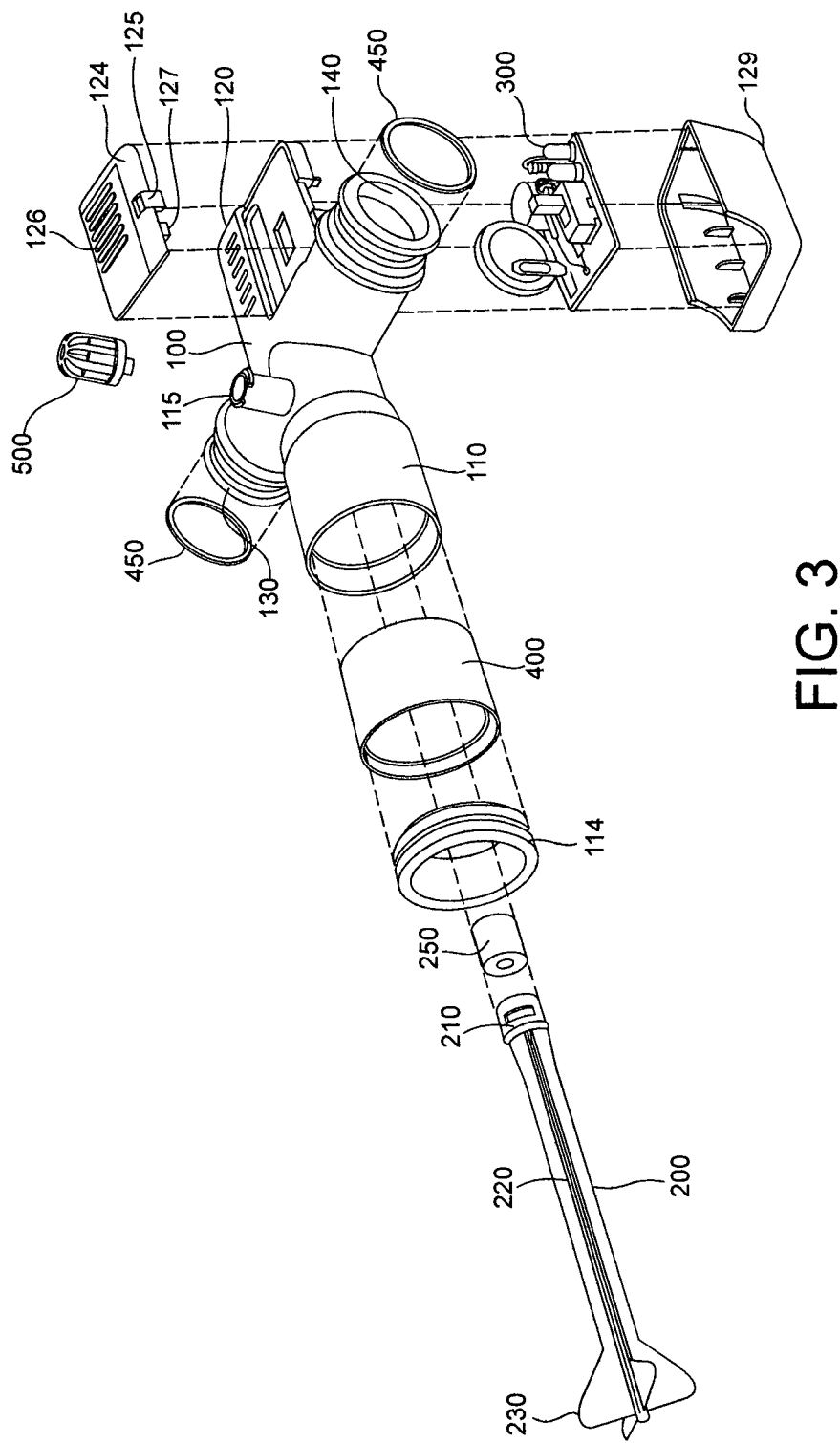
FIG. 3 is an exploded view of the multiple connector device for respiratory circuits with alarm due to disconnection shown in FIG. 1.
Figure 4:
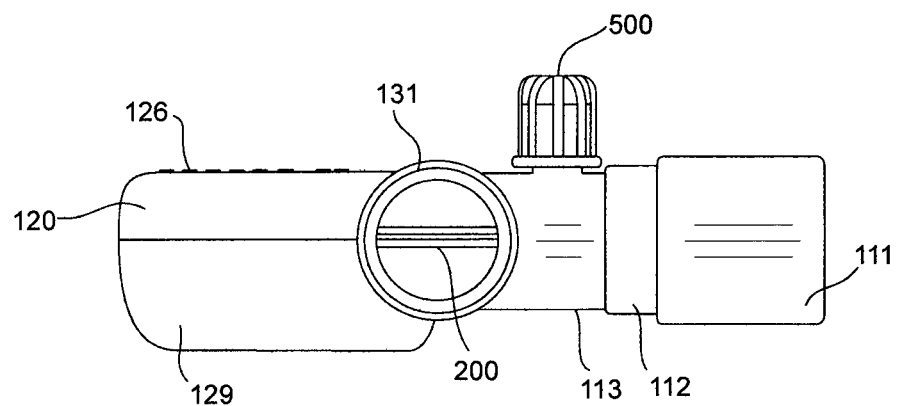
FIG. 4 is a right side view of the multiple connector device for respiratory circuits with alarm due to disconnection shown in FIG. 1.
Figure 5:
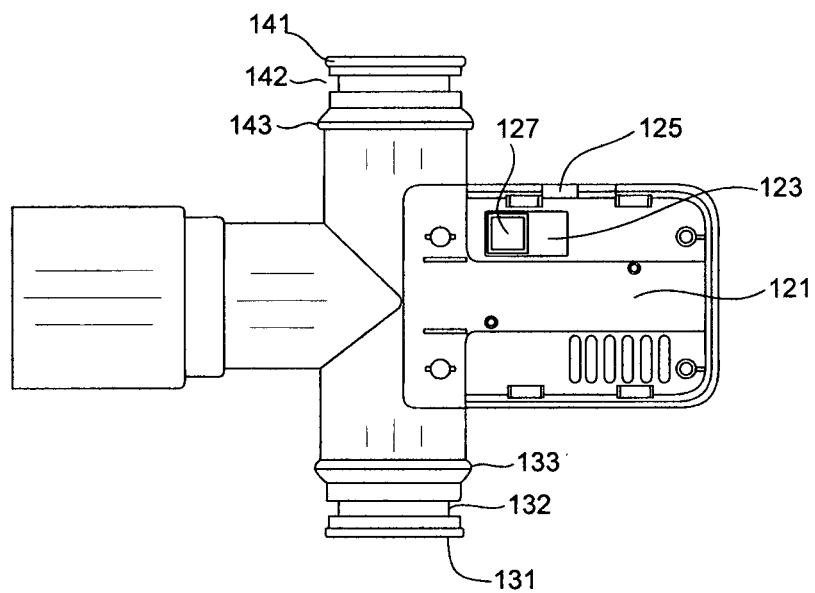
FIG. 5 is a bottom plan view of the main body that is part of the of the multiple connector device for respiratory circuits with alarm due to disconnection, in this figure the device is shown without the protecting cover of the lower vertical arm.

On the inner wall of the distal section 111 of the upper vertical arm 110, it is provided a first gasket 400 having the shape of a cylindrical ring as seen in FIG. 3. Said first gasket 400 has a length less than the total length of the distal section 111; the proximate part of the gasket is limited by the middle section 112, while the distal part of the gasket is limited by an inner retaining ring 114 which prevents any longitudinal movement of the gasket 400. It should be mentioned that once the first gasket 400 and the inner retaining ring 114 are situated in their final position, they have the same internal diameter. In a preferred embodiment, the first gasket 400 is made of silicone.

Figure 6:
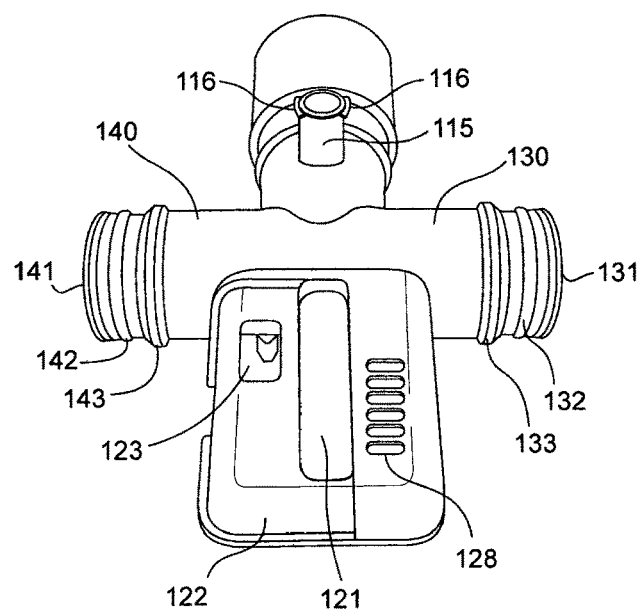
FIG. 6 is a front perspective view of the main body shown in FIG. 5, where the sliding cover has been removed for a better appreciation of the low-relief area.

With particular reference to FIG. 6, on the outer front surface of the proximate section 113, a hollow tube 115 having a cylindrical shape vertically protudes, the tube is threaded at its distal end, wherein the thread is used for securing a cap 500 whose structure will be described disclosed later. In a preferred embodiment, the thread of the tube 115 comprises at least two flat protrusions located on the periphery of its distal end the protrusions being opposite each other at an angle of 180°. Said tube 115 is preferably used for capnography of the user of the device 1000 of the present invention.

As it was described above, the lower vertical arm 120 has a square shape, inside which a guide conduct 121 extending from the inside of vertical upper arm 110 and longitudinally running along the total length of the lower vertical arm. The guide conduct 121 is aligned with the longitudinal axis of the upper vertical arm 110.

On the other hand, the upper face of the lower vertical arm 120 comprises a low-relief area 122 which extends about two thirds of the total area of the upper face of said lower vertical arm 120 and a non-relief area extending a third of the total surface of the upper face. In a preferred embodiment, the low-relief area 122 comprises: a hollow having a rectangular shape running throughout all its length and centrally located, wherein the guide conduct 121 passes through the rectangular hollow; and a rectangular opening 123 for accessing into the lower vertical arm 120.

Additionally, over the low-relief area 122, there is provided a sliding cover 124 that has the same peripheral contour as the low-relief area 122, the sliding cover slides longitudinally in both directions on said low-relief area 122. In order to be fastened to the low-relief zone 122, the sliding cover 124 has a locking tab 125, which is located at one of the lateral ends of the upper face and having an "L" form in a sectional cross view thereof. Preferably, the locking tab 125 is located at the left side end of the upper face, which is on the same side of the left lateral arm 140.

Further, on the upper face of the cover 124, there is provided a plurality of protrusions 126 which improve the support and holding of the sliding cover 124, when the last is manipulated by the user. From the inner face of the sliding cover 124, a rectangular tube 127, which coincides in position and in dimensions with the rectangular opening 123, is projected, by which said rectangular tube 127 can be inserted into the opening 123 when the sliding cover 124 is positioned over the low-relief area 122. In addition, on the non-relief area of the upper face of the lower arm 120, there is provided a grid 128 that allows acoustic communication between the inside of the lower vertical arm 120 ante the exterior of the device.

The lower face of the lower vertical arm 120 comprises a hollow protective cover 129 which has a form of a rectangular box without a lid. Said hollow protective cover 129 has a plurality of guide ribs (see FIG. 3) provided at the inner peripheral edge thereof, which besides give greater rigidity and strength once the cover is assembled to the main body 100, the guide ribs are used to keep in place the control element 300. In a preferred embodiment of the present invention, all the edges of the lower vertical arm 120 are rounded and without burrs to prevent the user that handles the multiple connector device 1000 gets hurt.

Figure 12:
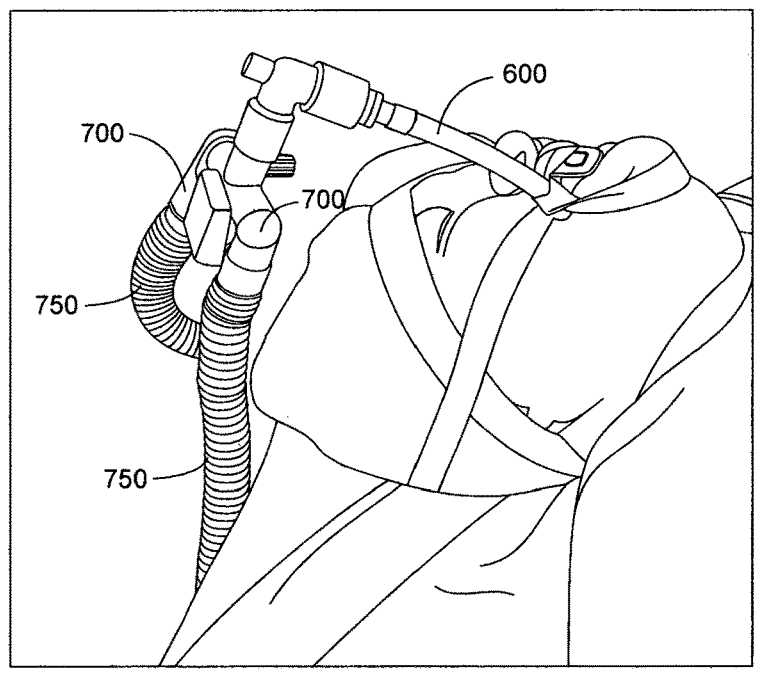
FIG. 12 is a schematic view showing how the multiple connector device for respiratory circuits with alarm due to disconnection is connected to a patient.

On the other hand, the right lateral arm 130 has a tubular form and has a constant inner diameter throughout all its length. At its distal end and on its outer surface of said right lateral arm 130 there is a first peripheral flange 131; in addition there is a first slit 132 adjacent to the first peripheral flange 131, the first slit serves for housing a second gasket 450 having an annular form. Also, adjacent to the first slit 132 and toward the center of the multiple connector device 1000, there is provided a first stop 133 which surrounds all the circumference of the right lateral arm 130. The structure and configuration of the right lateral arm 130 has the necessary elements for a proper coupling with a rotary-type connector 700 as shown in FIG. 12.

The left lateral arm 140 is a mirror image of the right lateral arm 130 and has the same elements, configuration and functionality of the right lateral arm 130, i.e., the left lateral arm 140 has a tubular form and has a constant inner diameter throughout all its length. At the distal end and on its outer surface, said left lateral arm 140 has a second peripheral flange 141 which is used for holding a connector 700. Adjacent to the second peripheral flange 141, it is located a second slit 142, which serves to receiving a second annular gasket 450. Also, adjacent to the second slit 142 towards the center of the multi connector device 1000, there is provided a second stop 143 that surrounds the circumference of the left lateral arm 140. In a similar manner as the right lateral arm 130, the left lateral arm allows a rotary-type connector 700 to be coupled.

Figure 7:
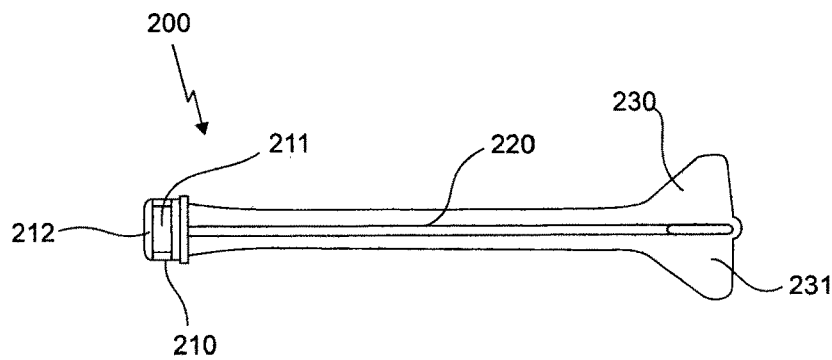
FIG. 7 is a right side view of the driving element that is part of the multiple connector device for respiratory circuits with alarm due to disconnection.
Figure 8:
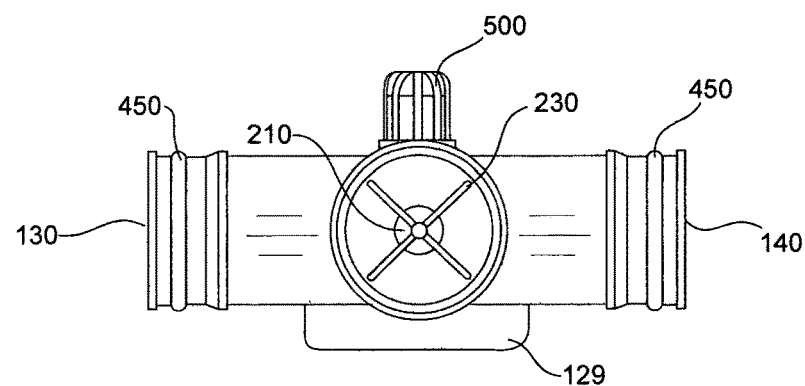
FIG. 8 is frontal view of the multiple connector device for respiratory circuits with alarm due to disconnection shown in FIG. 1.

Now reference is made to FIGS. 7 and 8, in said figures it is observed the driving element 200 that axially runs along the inside of the upper vertical arm 110 and the lower vertical arm 120 of the main body 100, the driving element has the shape of a flattened arrow and comprises a tip 210, a shaft 220 and a stabilizer 230. The tip 210 has a cylindrical shape and is hollow inside with the purpose of housing a sensing element 211 that is selected from a magnet, a capacitive piece and a magnetic core whose function will be described later. In order to the allow insertion and removal of the sensing element 211 that is housed inside said tip 210, the last has at least two windows 212 located in its lateral face. The orientation of the driving element 200 within the main body 100 is longitudinal and axial, that is to say, the tip 210 is coincident with the distal end of the lower vertical arm 120 while the stabilizer 230 is coincident with the distal end of the upper vertical arm 110, so that the driving element 200 is displaced longitudinally and axially between both distal ends.

In order to return the driving element 200 to its initial position, at the bottom of the guide conduct 121 there is provided a spring 250, which usually is extended, but is pressed by the driving element 200 when is longitudinally and axially displaced.

The stabilizing element 230, which is part of the driving element 200, comprises a plurality of blades 231 disposed symmetrically about the longitudinal axis of the driving element 200. In a preferred embodiment, the plurality of blades 231 are provided as a four blades, which are distributed in a radial and symmetrical manner (at 90° with respect to each other) along the longitudinal axis of the driving element 200.

Figure 9:
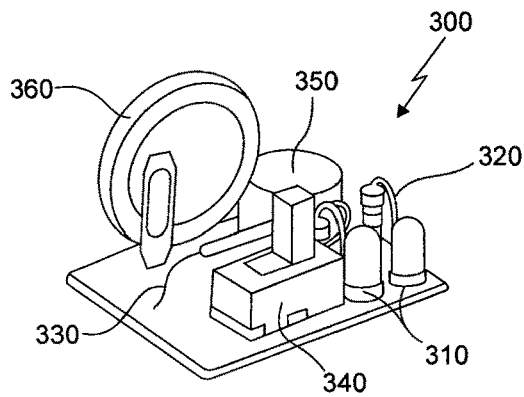
FIG. 9 is a left perspective view of the electronic board that is part of the multiple connector device for respiratory circuits with alarm due to disconnection.

Referring to FIG. 9, in the same there is observed the control element 300 that comprises an electronic board, which is located inside the lower vertical arm 120 of the main body 100. This control element 300 in conjunction with the driving element 200 are configured and include all those electronic components required for the correct operation of the multiple connector device 1000 of the present invention.

Said electronic components comprises a plurality of light emitting diodes 310 (LED) to indicate if the device is in "on" position, in addition the LEDS are the visual alarm of the apparatus; a plurality of resistors 320 operatively connected to the plurality of light emitting diodes 310 to regulate the electrical current and allow a proper performance; a central switch 330, which is used to activate or deactivate the audible and visual alarm of the multiple connector device 1000 in response to a signal that is received indicating the position of the driving element 200; a sliding switch 340 to manually turn on or turn off the multiple connector device 1000; a speaker 350 that constitutes the audible alarm when the device 1000 is disconnected and a battery 360 to energize all of the electronic components of the device 1000. In should be noted that the arrangement of the components over the electronic board is variable, with the exception of the central switch 330 and the sliding switch 340, since both of them are operatively connected with other elements of the multiple connector device 1000.

In the particularly case of the central switch 330, the same should maintain a parallel position relative to the guide conduct 121 of the lower vertical arm 120, in order to be activated or deactivated by means of the sensing element 211 located at the tip 210 of the driving element 200. The central switch 330 is located below the guide conduct 121 and in a parallel relation to the same.

As it was above mentioned, the sensing element 211 is selected from a magnet, a capacitive piece or a magnetic core. If the sensing element 211 is a magnet, it generates a magnetic effect that activates or deactivates the central switch 330. In the event that the sensing element is a capacitive piece, the same creates an effect that changes electrical capacitance; while if the sensing element is a magnetic core; it generates an effect that changes inductance which is used for detecting any disconnection.

On the other hand, the sliding switch 340 is coincident connected with the rectangular tube 127 of the sliding cover 124 in order to place the sliding switch 340 in "on" or "off" position by only sliding, up or down, said sliding cover 124.

Figure 10:
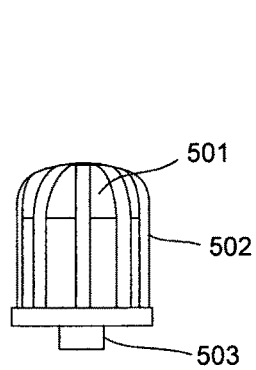
FIG. 10 is a lateral view of the cap that is part of the multiple connector device for respiratory circuits with alarm due to disconnection.
Figure 11:
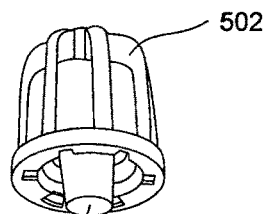
FIG. 11 is a bottom perspective view of the cap shown in FIG. 10.

With regard to FIGS. 10 and 11, it is shown a cap 500 that is placed on the hollow tube 115 of the upper vertical arm 110, that is part of the main body 100, the cap comprises a central body 501 having a cylindrical shape and being internally hollow, the cap is used when the device is not used in patient's capnography. From the top of the central body 501, there are providing a plurality of supports 502 radially disposed and downwardly running from the top of said central hollow body; in a preferred embodiment, the same are external longitudinal walls symmetrically and radially located along all the central body 501. At the inside of the central body 501 a solid post 503 downwardly runs from the upper wall, the post has a diameter that is slightly smaller than the inner diameter of the hollow tube 115 with this feature, it is allowed the insertion of said solid post 503 into said hollow tube 115. The inner wall of the central body is threaded to allow coupling thereof with the protrusions 116 of the hollow tube 115.

In connection with FIG. 12, the multiple connector device 1000 of the instant invention is used in those surgical procedures where it is required connecting an anesthesia circuit to a patient. For this, the multiple connector device 1000 is connected, by means of its upper vertical arm 110, to a device to control the airways in a patient 600 (such as an oxygen mask, a laryngeal mask, etc.), while the right lateral arm 130 and left lateral arm 140 are connected to connectors 700 of corrugated tubes 750 that are part of the anesthesia circuit. The first gasket 400 located in the inside of the distal section 111 of the upper vertical arm 110 allows a tight seal with the device to control the airways 600.

With respect to the connectors 700, these are of a rotary-type, which allows rotation of 360° of the corrugated tubes 750 coupled thereto about the longitudinal axis of the right lateral arm 130 and the left lateral arm 140; this feature gives the multiple connector device 1000 an increased orientation capacity with respect to the position of the device to control the airways 600.

In the case of the right lateral arm 130, a connector 700 is inserted through the distal end thereof until it stops with the first stop 133. Between the outer surface of the right lateral arm 130 and the inner surface of the connector 700, there is pressed the second gasket 450, achieving a tight seal where the gases flow through the corrugated tubes 750 to the inside of the multiple connector device 1000 avoiding leakage of the gases. The same happens in a similar manner in the left lateral arm 140, wherein a connector 700 is inserted through the distal end thereof until the connector is stopped by the second stop 143. Due to the presence of the second gasket 450, a tight seal is achieved between the left lateral arm 140 and the connector 700, thus preventing any gas leakage to the outside.

Figure 13:
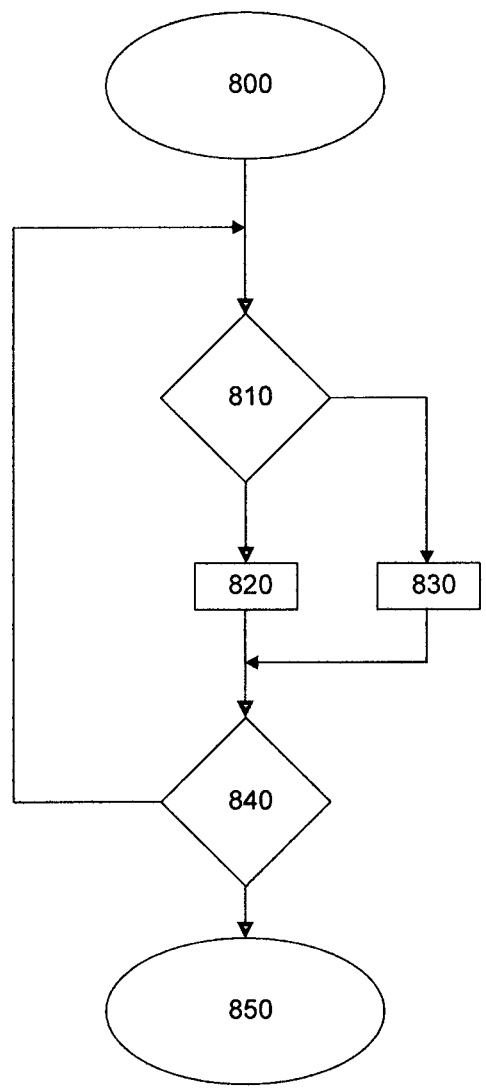
FIG. 13 is a flow chart where there are shown the operating stages of the multiple connector device for respiratory circuits with alarm due to disconnection.

In FIG. 13, a flowchart of the operation of the multiple connector device 1000 for respiratory circuits with alarm due to disconnection is shown.

In the initial step 800, the user of the device 1000 should place the sliding switch 340 to "on" position, displacing either up or down the sliding cover 124; when this occurs, the electronic elements of the control element 300 are powered by means of the electrical energy supplied by the battery 360, then a first diode of the plurality of light emitting diodes 310 turns on.

In the next step 810, the position of the driving element 200 into the guide conduct 121 modifies the status of the central switch 330 located on the control element 300. If there is not any external force pushing down the driving element 200, then the central switch 330 is in the "on" position and step 820 occurs; while, in case the driving element 200 is pressed by an external force enough to push the spring 250, then the central switch 330 is in "off" position and step 830 occurs.

In step 820, when the central switch 330 is in "on" position turns on the speaker 350 as well as a second diode of the plurality of light emitting diodes 310.

In step 830, when the central switch 330 is in "off" position, only the first diode of the plurality of light emitting diodes 310 stay in "on" position.

In the next step 840, if the user decides not to use the multi-connector device 1000, then the step 850 occurs, otherwise if the device is continuously used then the step 810 is repeated.

Finally, in step 850, the user should moving the sliding switch 340 to the "off" position moving the sliding cover in the opposite direction with respect the direction it was moved it in step 800; when this happens, the electronics elements of the control element 300 are depowered so that the first diode of the plurality of light emitting diodes 310 turns off.

It is worth mentioning that the external force pressing the driving element 200 is the force exerted by the coupling of the airway control device 600 into the upper vertical arm 110.

It will be apparent to one skilled in the art that the embodiments of the multiple connector device 1000 for respiratory circuits with alarm due to disconnection that has been explained in the detailed description and illustrated in the accompanying drawings is only illustrative but not limitative of the present invention, since numerous changes in details are possible without departing from the scope of the invention, such as changes to the main body shape, arrangement of the elements on the electronic board, the presence or absence of a tube for capnography, etc. Therefore, the present invention should not be considered as limited except as required by the prior art and the spirit of the appended claims.

What is claimed is:

1. A multiple connector device for respiratory circuits with alarm due to disconnection comprising:
   a main body that is hollow inside including four arms namely:
   an upper vertical arm, wherein a device for controlling the airway of a patient is connected;
   a lower vertical arm,
   a right lateral arm, and
   a left lateral arm, wherein corrugated tubes of an anesthesia circuit are connected to said right lateral arm and left lateral arm;
   a driving element housed inside the upper vertical arm and running into the lower vertical arm; the driving element is displaced inside said vertical upper arm and said lower vertical arm; and
a control element housed inside the lower vertical arm, and configured to indicate by a visual alarm when the connecter device is in an on position;
wherein the visual alarm and an audible alarm are activated in response to a signal that is received indicating that the airway is disconnected.

2. A multiple connector device for respiratory circuits with alarm due to disconnection according to claim 1, wherein the driving element has an arrow form comprising:
a tip having a cylindrical shape and hollow inside in order to house a sensing element;
a stem; and
a stabilizer including a plurality of blades arranged in a symmetrical manner around the longitudinal axis of the driving element.

3. A multiple connector device for respiratory circuits with alarm due to disconnection according to claim 2, wherein the tip includes at least two windows located in the side face thereof in order to allow insertion and removal of the sensing element.

4. A multiple connector device for respiratory circuits with alarm due to disconnection according to claim 2, wherein the tip of the driving element is coincident with the distal end of the lower vertical arm; while the distal end of the stabilizer coincides with the distal end of the upper vertical arm, so that the driving element is longitudinally and axially displaced between both ends of the arms.

5. A multiple connector device for respiratory circuits with alarm due to disconnection according to claim 2, wherein the upper arm comprises:
a distal section having a larger diameter;
a middle section located adjacent to the distal section and having an outer diameter and an inner diameter smaller with respect to those of the distal section; and
a proximate section located adjacent to the middle section and having an outer diameter smaller than that of the middle section but having an inner diameter equal to that of the middle section, said proximate section extending until the center of the main body.

6. A multiple connector device for respiratory circuits with alarm due to disconnection according to claim 5, wherein, on the inner wall of the distal section of the upper vertical arm, there are provided a first gasket disposed on the middle section; and an inner retaining ring that prevents longitudinal movement of said first gasket.

7. A multiple connector device for respiratory circuits with alarm due to disconnection according to claim 5, further comprising a hollow tube that is provided on the outer front surface of the proximate section, the hollow tube being used for capnography measurements; and
a cap that covers said hollow tube when the same is not in use.

8. A multiple connector device for respiratory circuits with alarm due to disconnection according to claim 7, wherein the hollow tube has a cylindrical form and is threaded at its distal end; while the cap comprises:
a central hollow cylindrical body that is threaded inside;
plurality of supports radially disposed and downwardly running from the top of said central hollow body; and
a solid post which projects downwardly from the interior of the inner portion of said central body to be inserted into the hollow tube.

9. A multiple connector device for respiratory circuits with alarm due to disconnection according to claim 8, wherein the thread of the hollow tube comprises at least two flat protrusions located on the periphery of its distal end, the protrusions being opposite each other at 180°.

10. A multiple connector device for respiratory circuits with alarm due to disconnection according to claim 1, wherein the lower vertical arm further comprises a guide conduct extending from the inside of vertical upper arm and longitudinally running along the total length of the vertical lower arm, said guide duct being aligned with the longitudinal axis of the upper vertical arm.

11. A multiple connector device for respiratory circuits with alarm due to disconnection according to claim 10, wherein the upper face of the lower vertical arm comprises:
a low-relief area including a rectangular opening that is centrally located on the low-relief area, through which the guide conduct passes;
a rectangular hollow to access the inside of the lower vertical arm; and
a sliding cover located on the entire outer surface, which slides longitudinally in both directions on said low-relief area; and
a no relief area including a grid that is located adjacent to the low-relief area and allows audio communication between the inside of the lower vertical arm and the outer of the device.

12. A multiple connector device for respiratory circuits with alarm due to disconnection according to claim 11, wherein the sliding cover comprises:
an upper face;
a locking tab to attach the sliding cover to the low-relief area, the latching tab being located on the outer side end of the front section and having a L-form in a cross sectional view;
a plurality of protrusions located on the upper face;
a rectangular tube projecting from the inner face of the sliding cover, the last coincides in position and has the same dimensions to the rectangular opening of the low-relief zone so that said rectangular tube is allowing to be inserted into the opening when the sliding cover is positioned over the low-relief area.

13. A multiple connector device for respiratory circuits with alarm due to disconnection according to claim 11, wherein the lower face of the lower vertical arm comprises a hollow protective cover that has the shape of a rectangular box which includes a plurality of guide reinforcements at its inner peripheral edge to hold the control element in place.

14. A multiple connector device for respiratory circuits with alarm due to disconnection according to claim 10, wherein the guide conduct includes a spring that is housed therein.

15. A multiple connector device for respiratory circuits with alarm due to disconnection according to claim 1, wherein the right lateral arm has a first peripheral flange located at its distal end and on its outer surface;
a first slot located adjacent the first peripheral flange, which serves for housing a second ring-shaped gasket; and
a first stop located adjacent to the first slot towards the center of the connector device and which surrounds the circumference of said right lateral arm.

16. A multiple connector device for respiratory circuits with alarm due to disconnection according to claim 1, wherein the left lateral arm has a second peripheral flange at its distal end and on its outer surface thereof;
a second slot located adjacent to the second peripheral flange, which serves for housing a second gasket; and a second stop located adjacent to the second recess towards the center of the connector device and which surrounds the circumference of the left lateral arm.

17. A multiple connector device for respiratory circuits with alarm due to disconnection according to claim 1, wherein the control element is an electronic board which includes:
   a plurality of light emitting diodes to indicate if the device is on, the diodes comprising the visual alarm;
   a plurality of resistors operatively connected to the plurality of light emitting diodes for regulating the electrical current;
   a central switch to activate or deactivate the visual and the audible alarm of the multiple connector device in response to a signal received from the position of the driving element;
   a sliding switch to manually turn the device on or off;
   a speaker that is the audible alarm when the device is disconnected; and
   a battery to power the electronics components of the device.

18. A multiple connector device for respiratory circuits with alarm due to disconnection according to claim 17, wherein the central switch is activated or deactivated by the sensing element located at a tip of the driving element.

19. A multiple connector device for respiratory circuits with alarm due to disconnection according to claim 17, wherein the sliding switch is coincident with a rectangular tube of the sliding cover in order to allow the sliding switch to be turned "on" or "off" only by the sliding up or down movement of said sliding cover.

20. A multiple connector device for respiratory circuits with alarm due to disconnection according to claim 1, wherein the sensing element is selected from a magnet, a capacitive piece or a magnetic core.

* * * * *